United States Patent
Dinarello

(10) Patent No.: US 11,517,554 B2
(45) Date of Patent: Dec. 6, 2022

(54) METHOD FOR PREVENTING OR TREATING ALZHEIMER'S DISEASE

(71) Applicant: OLATEC THERAPEUTICS LLC, New York, NY (US)

(72) Inventor: Charles A. Dinarello, Boulder, CO (US)

(73) Assignee: OLATEC THERAPEUTICS LLC, New York, NY (US)

( * ) Notice: Subject to any disclaimer, the term of this patent is extended or adjusted under 35 U.S.C. 154(b) by 182 days.

(21) Appl. No.: 16/942,312

(22) Filed: Jul. 29, 2020

(65) Prior Publication Data
US 2020/0352897 A1    Nov. 12, 2020

Related U.S. Application Data

(63) Continuation of application No. PCT/US2019/016012, filed on Jan. 31, 2019.

(60) Provisional application No. 62/624,637, filed on Jan. 31, 2018.

(51) Int. Cl.
*A61K 31/275* (2006.01)
*A61P 25/28* (2006.01)
*A61K 9/00* (2006.01)

(52) U.S. Cl.
CPC .......... *A61K 31/275* (2013.01); *A61K 9/0053* (2013.01); *A61P 25/28* (2018.01)

(58) Field of Classification Search
CPC .. A61K 31/275; A61K 9/0019; A61K 9/0053; A61K 9/008; A61P 25/28
See application file for complete search history.

(56) References Cited

U.S. PATENT DOCUMENTS

2012/0157524 A1\* 6/2012 St. Laurent ............. A61P 21/00 558/312
2017/0119725 A1   5/2017 St. Laurent

FOREIGN PATENT DOCUMENTS

| WO | 2012082718 A2 | 6/2012 |
| WO | 2014066318 A1 | 5/2014 |
| WO | WO-2014194166 A1 \* | 12/2014 ........... A61K 31/427 |
| WO | 2015165961 A1 | 11/2015 |
| WO | 2016138425 A1 | 9/2016 |

OTHER PUBLICATIONS

Stanford Health care https://stanfordhealthcare.org/medical-conditions/brain-and-nerves/alzheimers-disease/prevention.html accessed Apr. 8, 2022.\*
WebMD https://www.webmd.com/alzheimers/guide/understanding-alzheimers-disease-prevention accessed Apr. 8, 2022.\*
Mayo Clinic https://www.mayoclinic.org/diseases-conditions/alzheimers-disease/expert-answers/alzheimers-prevention/faq-20058140 accessed Apr. 8, 2022.\*
Daniels et al. 'Fenamate NSAIDs inhibit the NLRP3 inflammasome and protect against Alzheimer's disease in rodent models', Nature Communications, 2016, vol. 7:12504, pp. 1-10.
International Search Report dated Apr. 15, 2019 of PCT/US2019/016012 (2 pages).
Marchetti et al. 'OL T1177, a Beta-sulfonyl nitrile compound, safe in humans, inhibits the NLRP3 inflammasome and reverses the metabolic cost of inflammation',PNAS, 2018, vol. 115(7), E1530-E1539; Published online Jan. 29, 2018; doi/10.1073/pnas.1716095115 (34 pages).
Griffin, W. et al. "Brain interleukin 1 and S-100 immunoreactivity are elevated in Down syndrome and Alzheimer disease" PNAS-USA; 1989, vol. 86, pp. 7611-7615.
Heneka, M. et al. "NLRP3 is activated in Alzheimer's disease and contributes to pathology in APP/PS1 mice" Nature, 2013, vol. 493, pp. 674-678 with 3 supplemental pages.
Iadecola, C. "Dangerous Leaks: Blood-Brain Barrier Woes in the Aging Hippocampus" Neuron, 2015, vol. 85, pp. 231-233.
Kitazawa, M. et al. "Blocking IL-1 Signaling Rescues Cognition, Attenuates Tau Pathology, and Restores Neuronal β-Catenin Pathway Function in an Alzheimer's Disease Model" J. Immunol. 2011, vol. 187, pp. 6539-6549.
Skouras, Damaris. Interview with Brett Johnson. "Damaris Skouras—CEO of Olatec on Treating Inflammation" OneMedMarket News & Information Center, Dec. 23, 2016 (Dec. 23, 2016), pp. 1-4.

\* cited by examiner

*Primary Examiner* — Kara R McMillian
(74) *Attorney, Agent, or Firm* — Perkins Coie LLP; Viola Kung

(57) ABSTRACT

The present invention is directed to a method for preventing and/or treating Alzheimer's disease. The method comprises administering to a subject in need thereof an effective amount of dapansutrile. The method reduces neuroinflammation and improves the cognitive functions such as learning and memory processes of the subject. Dapansutrile can be administered to the subject orally at a dose of 100-2000 mg/day for 3 months to 5 years or longer.

10 Claims, 4 Drawing Sheets

METHOD FOR PREVENTING OR TREATING ALZHEIMER'S DISEASE

This application is a continuation of PCT/US2019/016012, filed Jan. 31, 2019; which claims the benefit of U.S. Provisional Application No. 62/624,637, filed Jan. 31, 2018. The contents of the above-identified applications are incorporated herein by reference in their entirety.

FIELD OF THE INVENTION

The present invention relates to using dapansutrile (3-methanesulfonylpropionitrile), or its pharmaceutically acceptable solvate for preventing and/or treating Alzheimer's disease.

BACKGROUND

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans.

Although Alzheimer's disease develops differently for every individual, there are many common symptoms. Early symptoms are often mistakenly thought to be age-related concerns, or manifestations of stress. In the early stages, the most common symptoms are motor decline and difficulty in remembering recent events, known as short-term memory loss (Buchman et al, Exp Rev Neurother, 11:665-76, 2011). When AD is suspected, the diagnosis is usually confirmed with tests that evaluate behavior and thinking abilities, often followed by a brain scan if available. As the disease advances, symptoms can include confusion, irritability, aggression, mood swings, trouble with language, and long-term memory loss. As the person's condition declines, he/she often withdraws from family and society. Gradually, bodily functions are lost, ultimately leading to death.

The brains of individuals with AD exhibit characteristic lesions termed amyloid plaques, amyloid angiopathy (amyloid deposits in blood vessels) and neurofibrillary tangles, as well as neuroinflammation. Large numbers of these lesions, particularly amyloid plaques and neurofibrillary tangles, are generally found in several areas of the human brain important for memory and cognitive function in patients with AD. At present, a definitive diagnosis of AD usually requires observing the aforementioned lesions in the brain tissue of patients who have died with the disease or, rarely, in small biopsied samples of brain tissue taken during an invasive neurosurgical procedure.

Neuroinflammation is inflammation of the nervous tissue. It may be initiated in response to a variety of cues, including infection, traumatic brain injury, toxic metabolites, or autoimmunity. In the central nervous system (CNS), including the brain and spinal cord, microglia are the resident innate immune cells that are activated in response to these cues. The CNS is typically an immunologically privileged site because peripheral immune cells are generally blocked by the blood-brain barrier (BBB), a specialized structure composed of astrocytes and endothelial cells. However, circulating peripheral immune cells may surpass a compromised BBB and encounter neurons and glial cells expressing major histocompatibility complex molecules, perpetuating the immune response. Although the response is initiated to protect the central nervous system from the infectious agent, the effect may be toxic and widespread inflammation as well as further migration of leukocytes through the blood-brain barrier.

The principal chemical constituent of the amyloid plaques and amyloid angiopathy characteristic of AD is an approximately 4.2 kilodalton protein of about 39-43 amino acids designated the β-amyloid peptide. β-Amyloid peptide is a small fragment of a much larger amyloid precursor protein (APP), derived from cleavage of APP by protease systems, collectively termed secretases. APP is an integral membrane protein expressed in many tissues and concentrated in the synapses of neurons. Its primary function is not known, though it has been implicated as a regulator of synapse formation, neural plasticity and iron export. APP is best known as the precursor molecule whose proteolysis generates beta amyloid (Aβ), a 37 to 49 amino acid peptide whose amyloid fibrillar form is the primary component of amyloid plaques found in the brains of Alzheimer's disease patients. APP is first cleaved by β secretase to yield a β-stub, which is then cleaved by γ secretase to yield a β-amyloid fragment that is secreted.

Elevated Interleukin-1 beta (IL-1β) levels, an apical pro-inflammatory mediator in acute and chronic inflammation and a powerful inducer of the innate immune response, has been reported in brains of AD patients since 1989 (Proc Natl Acad Sci USA 86:7611-5). Kitzawa et al (J Immunol. 2011, 187: 6539-6549) report that blocking interleukin-1 signaling rescues cognition, attenuates tau pathology, and restores neuronal β-catenin pathway function in an AD model. Heneka et al (Nature 2013, 493: 7434) report that NLRP3 is activated in AD and contributes to pathology in APP/PS1 mice.

There are recent studies suggesting that part of the pathogenesis of AD is a "leaky blood brain barrier" (Iadecola, Neuron, 85: 231-233, 2015). One of the most argued concepts of the pathogenesis of AD is whether there is breakdown of the barrier, allowing inflammatory cells to migrate into the hippocampus (memory center). As Iadecola writes in his Commentary, there are now data to support a breakdown in the barrier associated with cognitive dysfunction.

There is a need to develop methods and compositions for prevention and treatment of AD.

DETAILED DESCRIPTION OF THE INVENTION

Figure 1B:
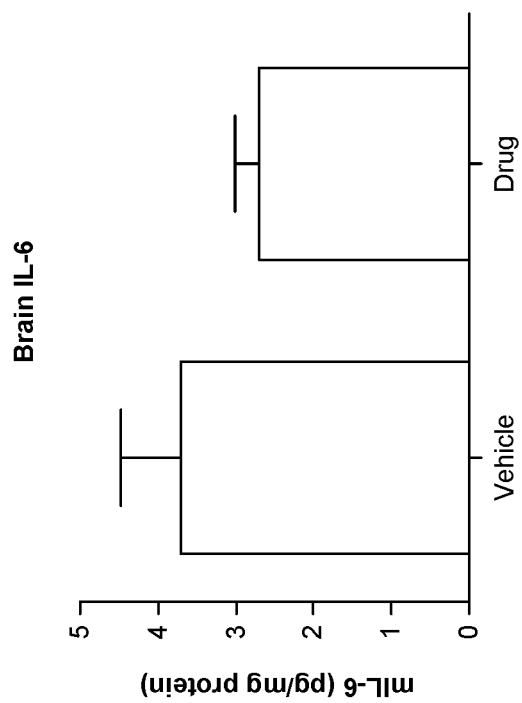
FIGS. 1A and 1B show brain levels of IL-6 and MPO in ex vivo samples of vehicle and dapansutrile-treated mice, after IL-1β intraperitoneal challenge.

The inventor has discovered that dapansutrile, which consistently reduces the levels of pro-inflammatory cytokines, including IL-1β and IL-6, in several whole animal models of local and systemic inflammation, is effective in treating Alzheimer's disease (AD), and improving motor/behavior dysfunction in AD. The inventor has discovered that dapansutrile is effective in reducing the spontaneous production of IL-1β, reducing the induction of IL-6, reducing systemic and neuroinflammation. In vitro, ex vivo and in vivo studies have demonstrated that dapansutrile inhibits the processing and release of IL-1β, but not the synthesis of the IL-1β precursor. The inventor believes that by treating the peripheral cells with dapansutrile, spontaneous IL-1β is reduced, which results in a lower level of inflammation in blood-derived microglia. Dapansutrile preserves the body's immune surveillance by not suppressing constitutive cytokines and to protect from cell death. Dapansutrile does not directly inhibited TNF-α, IL-1α or global cytokines, and thus its off-target activity is minimal.

The inventor discovered that one view for the pathogenesis of Alzheimer's disease is that the tight junction of the endothelial cells that essentially form the blood brain barrier becomes less effective with AD, which allows for molecules that should never enter the hippocampus, now to enter. The inventor believes that IL-1β is one of the molecules that not only contributes to the "leak" but also that the "leaky blood brain barrier" allows IL-1β (and several cytokines) to enter the hippocampal area. The presence of IL-1β in brain causes inflammation to take place and amyloid be synthesized. Increased synthesis of amyloid is one of the pathogenic properties of Alzheimer's disease. By reducing the systemic and brain levels of IL-1β, dapansutrile reduces IL-1β mediated systemic inflammation and neuroinflammation, and is effective in preventing and treating AD.

The present invention is directed to a method for preventing and/or treating Alzheimer's disease. The method comprises the step of administering to a subject in need thereof an effective amount of dapansutrile, or a pharmaceutically acceptable solvate thereof.

Compound

3-Methanesulfonylpropionitrile, also known as dapansutrile, is a small molecule, whose structure is shown below.

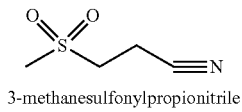

3-methanesulfonylpropionitrile

The present invention uses dapansutrile, or a pharmaceutically acceptable solvate thereof "Solvates," as used herein, are addition complexes in which the compound is combined with an acceptable co-solvent in some fixed proportion. Co-solvents include, but are not limited to, water, acetic acid, ethanol, and other appropriate organic solvents.

One of the hydrogen, oxygen, sulfur, and nitrogen atoms of dapansutrile is optionally substituted with a respective isotope that includes, but not limited to $^2H$ (deuterium), $^3H$ (tritium), $^{13}C$, $^{14}C$, $^{15}N$, $^{17}O$, $^{18}O$, and $^{35}S$. A non-radioactive or stable isotope such as $^2H$ (deuterium), $^{13}C$, $^{15}N$, $^{17}O$, or $^{18}O$ is preferred, with $^2H$ (deuterium) is more preferred.

Pharmaceutical Compositions

The present invention provides pharmaceutical compositions comprising one or more pharmaceutically acceptable carriers and an active compound of dapansutrile, or a pharmaceutically acceptable salt, or a solvate thereof. The active compound or its pharmaceutically acceptable solvate in the pharmaceutical compositions in general is in an amount of about 0.01-20%, or 0.05-20%, or 0.1-20%, or 0.2-15%, or 0.5-10%, or 1-5% (w/w), for a topical formulation; about 0.1-5% for an injectable formulation, 0.1-5% for a patch formulation, about 1-90% for a tablet formulation, and 1-100% for a capsule formulation. The active compound used in the pharmaceutical composition in general is at least 90%, preferably 95%, or 98%, or 99% (w/w) pure.

In one embodiment, the pharmaceutical composition is in a dosage form such as tablets, capsules, granules, fine granules, powders, syrups, suppositories, injectable solutions, patches, inhalers, or the like. In another embodiment, the active compound is incorporated into any acceptable carrier, including creams, gels, lotions or other types of suspensions that can stabilize the active compound. The above pharmaceutical composition can be prepared by conventional methods.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cysteine, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and poloxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylenediaminetetraacetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of the active compound may contain other excipients that have no bioactivity and no reaction with the active compound. Excipients of a tablet may include fillers, binders, lubricants and glidants, disintegrators, wetting agents, and release rate modifiers. Binders promote the adhesion of particles of the formulation and are important for a tablet formulation. Examples of binders include, but not limited to, carboxymethylcellulose, cellulose, ethylcellulose, hydroxypropylmethylcellulose, methylcellulose, karaya gum, starch, starch, and tragacanth gum, poly(acrylic acid), and polyvinylpyrrolidone.

For example, a patch formulation of the active compound may comprise some inactive ingredients such as 1,3-butylene glycol, dihydroxyaluminum aminoacetate, disodium edetate, D-sorbitol, gelatin, kaolin, methylparaben, polysorbate 80, povidone (polyvinylpyrrolidone), propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethyl ether.

Topical formulations including the active compound can be in a form of gel, cream, lotion, liquid, emulsion, ointment, spray, solution, and suspension. The inactive ingredients in the topical formulations for example include, but not limited to, lauryl lactate (emollient/permeation enhancer), diethylene glycol monoethyl ether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

Pharmaceutical compositions of the invention can be in the form of an aerosol suspension of respirable particles comprising the active compound, which the subject inhales. The respirable particles can be liquid or solid, with a particle size sufficiently small to pass through the mouth and larynx upon inhalation. In general, particles having a size of about 1 to 10 microns, preferably 1-5 microns, are considered respirable.

Method of Use

The present invention is directed to a method of preventing and/or treating Alzheimer's disease (AD). The method comprises the steps of first identifying a subject suffering from AD or likely to develop AD, and administering to the subject an effective amount of the active compound dapansutrile. "An effective amount," as used herein, is the amount effective to prevent or treat AD by ameliorating the pathological condition or reducing the symptoms of AD.

In one embodiment, the method reduces or alleviates the disease symptoms and improves the cognitive and motor functions of a subject suffering from AD. The subject may be identified by clinical signs of memory loss, or a brain scan that diagnoses AD. The method improves symptoms of confusion, irritability, aggression, mood swings, trouble with language, and/or long-term memory loss in a patient. The method also improves the learning and memory processes in a subject.

In another embodiment, the method provides prophylactic use of dapansutrile, which stops or slows down the disease progression. For prophylactic use, the subject is selected by family history, genetic screening, and/or early signs of memory loss. The method improves the cognitive and or motor functions of the subject and improves the learning and memory processes.

In neuroscience, long-term potentiation (LTP) is a persistent strengthening of synapses based on recent patterns of activity. These are patterns of synaptic activity that produce a long-lasting increase in signal transmission between two neurons. Synaptic failure in AD is largely reflected by impaired long-term synaptic plasticity in terms of long-term potentiation (LTP). LTP is widely considered one of the major cellular mechanisms that underlies learning and memory. The present invention provides an improvement in LTP.

The inventor has demonstrated that dapansutrile reduced the production of the two major cytokines associated with the pathogenesis of AD in brain: IL-1$\beta$ and IL-6. That is, after 3 months treatment with dapansutrile of AD transgenic mice, there is a significant reduction in the pro-inflammatory cytokine levels of IL-1$\beta$ and IL-6 in brain.

In the performance of the Morris water maze test, AD transgenic animals showed cognitive learning deficits compared to wildtype mice. In contrast, AD transgenic animals treated with a proper dose of dapansutrile performed as good as wildtype animals. LTP measurements showed a similar effect. AD transgenic animals showed impaired LTP, but AD transgenic animals treated with a proper dose of dapansutrile exhibited comparable LTP to wildtype animals.

The pharmaceutical composition of the present invention can be applied by systemic administration or topical administration. Systemic administration includes oral, parenteral (such as intravenous, intramuscular, subcutaneous or rectal), inhalation, and other systemic routes of administration. In systemic administration, the active compound first reaches plasma and then distributes into target tissues.

Dosing of the composition can vary based on the extent of the injury and each patient's individual response. For systemic administration, plasma concentrations of the active compound delivered can vary; but are generally $1\times10^{-10}$-$1\times10^{-4}$ moles/liter, and preferably $1\times10^{-8}$-$1\times10^{-5}$ moles/liter.

In one embodiment, the pharmaceutical composition is administrated orally to the subject. The dosage for oral administration is generally at least 0.1 mg/kg/day and less than 100 mg/kg/day. For example, the dosage for oral administration is 0.1-100 or 0.5-50 mg/kg/day, and preferably 1-10 or 1-20 mg/kg/day for a human subject. For example, the dosage for oral administration is 20-1000 mg/day or 100-2000 mg/day, and preferably 20-500, 25-200, 50-500, 50-200, 100-600, 100-400, 100-800, 200-800, 400-800, 400-1200, 500-2000, or 800-2000 mg/day for a human subject.

In one embodiment, the pharmaceutical composition is administrated intravenously to the subject. The dosage for intravenous bolus injection or intravenous infusion is generally 0.03 to 20 and preferably 0.03 to 10 mg/kg/day.

In one embodiment, the pharmaceutical composition is administrated subcutaneously to the subject. The dosage for subcutaneous administration is generally 0.3-20, and preferably 0.3-3 mg/kg/day.

In one embodiment, the pharmaceutical composition is administered by inhalation. Methods of inhalation include liquid instillation, instillation as a pressurized fluid preparation via metered dose inhaler or equivalent, or inhalation of an aerosolized solution via nebulizer, inhalation of dry powder, and directing soluble or dried material into the air stream during mechanical ventilation. The surface concentrations of the active compound delivered via inhalation can vary, but are generally $1\times10^{-10}$-$1\times10^{-4}$ moles/liter, and preferably $1\times10^{-8}$-$1\times10^{-5}$ moles/liter.

Those of skill in the art will recognize that a wide variety of delivery mechanisms may be suitable for the present invention.

Dapansutrile is well-tolerated in animals and humans, and therefore the present method is suitable for chronic treatment of an AD subject. The subject can be treated daily or every 1-3 days. The duration of treatment can be from 1 month to 3 months, 1 month to 6 months, 1 month to 1 year, 1 month to 2 years, 1 month to 5 years, 3 months to 6 months, 3 months to 1 year, 3 month to 2 years, 3 months to 5 years, 6 months to 1 year, 6 month to 2 years, 6 months to 5 years, 6 months to 10 years, or up to the lifetime of the subject.

Dapansutrile can be used for intermittent dosing. For example, the subject can be treated for 1-5 years on dapansutrile, and then off dapansutrile for 1-5 years, and then the dosing on/off regimen is repeated.

The present invention is useful in treating a mammal subject, such as humans, horses, and dogs. The present invention is particularly useful in treating humans.

The following examples further illustrate the present invention. These examples are intended merely to be illustrative of the present invention and are not to be construed as being limiting.

EXAMPLES

Example 1

Off-Target Activity

To investigate potential off-target activity of dapansutrile, secondary pharmacological effects were assessed through in vitro screening assays. Dapansutrile has no inhibitory effect on cytokine production via the AIM2 or NLRC4 inflammasome pathways, and dapansutrile shows no inhibition of pro-IL-1 or pro-IL-18. An evaluation of 68 critical transmembrane and soluble receptors, ion channels and monoamine transporters were performed for off-target effects of dapansutrile. An additional 69 receptors and enzymes were evaluated with dapansutrile for potential activity in a follow-on study that focused on enzymes involved in inflammatory cascades. A single identified target, the PDE4 enzyme, was inhibited in a concentration range of ≥100 μM (13 μg/mL) and was dose-responsive for effect, but subsequent studies were not conclusive. No other effects were noted in the screening assays, including no direct effects on COX-1 or COX-2 and no interaction with opioid receptors.

Example 2

Levels of IL-6 and MPO after Treatment

Figure 1A:
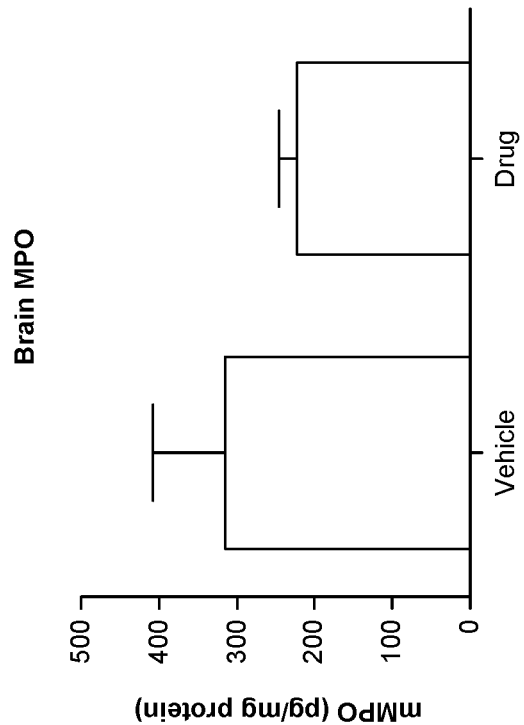

Mice were treated with 200 mg/kg dapansutrile (OLT1177™) for 8 injections over 4 days. Mice were trained on a rotarod on day 3. Twelve hours after the last injection, mice were run on the rotarod for distance. One hour after the rotarod, mice were challenged with 60 ng IL-1β intraperitoneally; mice were then sacrificed 4 hours later. Whole blood, plasma, brain, and lung of the mice were collected. Whole blood was cultured, plasma was frozen. Brain was processed for cytokine analysis. ELISA measurements of cytokines were conducted for all samples and the results are shown in FIGS. 1A and 1B. Each group had N=5.

Ex vivo samples were obtained from the brain of mice treated with vehicle or dapansutrile and subjected to exhaustive exercise. After IL-1β stimulation, the samples showed reduced levels of IL-6 and myeloperoxidase (MPO) in the brain (FIGS. 1A and 1B). In addition, the levels of systemic IL-1β, IL-6 and MPO after IL-1β stimulation were also reduced in treated mice (data not shown here).

Example 3

Treatment Protocol of Transgenic Mice Treated with Dapansutrile

APP/PS1 mice express a human amyloid precursor protein and human presenilin-1, each carrying mutations associated with familial AD, leading to age related deposition of Aβ, with accompanying neuroinflammation and cognitive impairment.

In the study design, 6-month-old wild-type (WT), and AD transgenic APP/PS1[deltaE9] mice were treated with oral dapansutrile via feed pellets ad libitum (approximately 0, 50 or 100 mg/kg/day based on feed concentrations of 0, 3.75 or 7.5 g/kg and food consumption of 4 g/day) for the treatment duration of 3 months. At 9 months old, behavior testing of the mice was performed. In addition, the brains of the mice were extracted, and blood samples were collected. The brains of the mice from each group were performed for electrophysiological and neuronal morphological analysis, cytokine levels and other assays.

Example 4

Cytokine Levels of Brain Homogenates

Figure 2A:
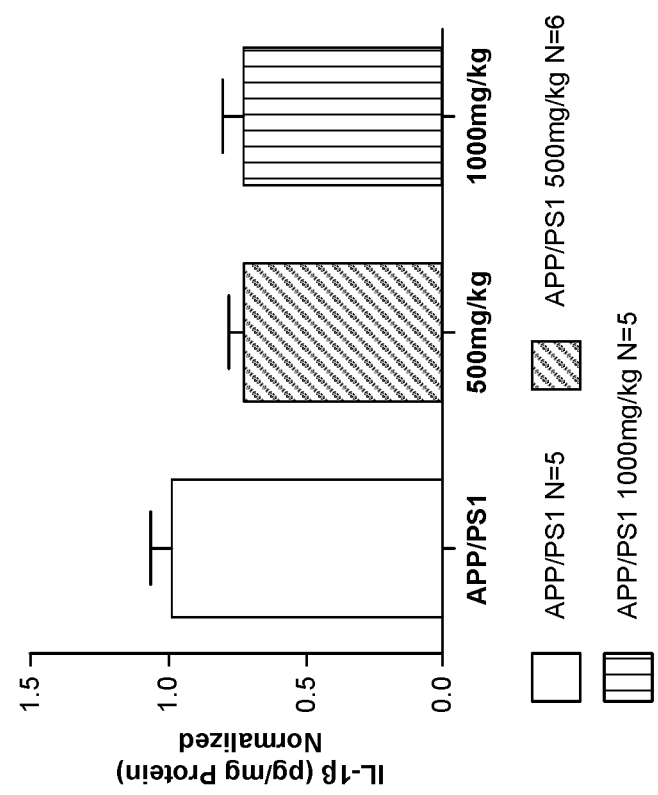
FIG. 2A shows that the levels of pro-inflammatory cytokines IL-6 were reduced in brain lysate of transgenic AD transgenic mice (APP/PS1 strain) treated with 1000 mg/kg/day of dapansutrile.
Figure 2B:
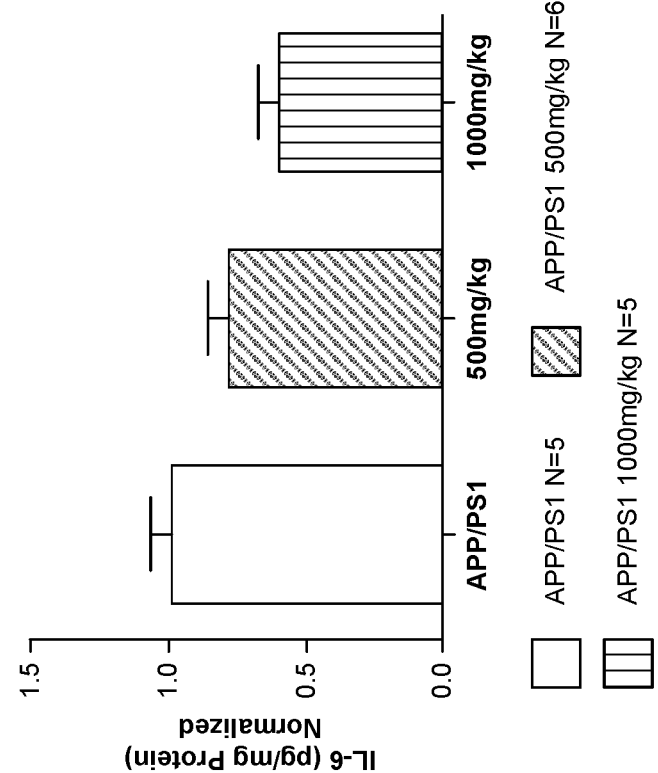
FIG. 2B shows that the levels of pro-inflammatory cytokines IL-1β were reduced in brain lysate of AD transgenic mice treated with both 500 mg/kg/day and 1000 mg/kg/day doses of dapansutrile.

One hemisphere of each mouse was homogenized in STKM-buffer and centrifuged for 10 min at 4° C. with 13,000 g. The supernatant of the brain lysate was collected and measured for pro-inflammatory mediators IL-6 and IL-1β by ELISA by diluting the sample 1:2. The results shown in FIGS. 2A and 2B demonstrate a reduction in neuroinflammation. The IL-6 levels in brain lysate were reduced in APP/PS1 mice treated with dapansutrile at medium dose (1000 mg/kg/day, p value=0.0035) compared to APP/PS1 mice fed with control food that did not contain dapansutrile (FIG. 2A). The IL-1β levels were reduced in APP/PS1 mice treated with dapansutrile at a low dose (500 mg/kg/day, p value=0.0287) and a medium dose (1000 mg/kg/day, p value=0.0368) compared to APP/PS1 mice fed with control food (FIG. 2B)

Example 5

Morris Water Maze Test

Objective: The Morris Water Maze (MWM) test was performed to test if APP/PS1 animals treated with dapansutrile can reduce the cognitive impaired phenotype of APP/PS1 animals when compared to both the wildtype animals and the APP/PS1 control animals without treatment.

An open-field water-maze procedure in which mice learn to escape from opaque water onto a hidden platform is a well-established model for testing cognitive functions in mice (Morris, J Neurosci Methods. 11:47-60, 1984).

Spatial memory formation and retention were assessed using the Morris water maze (MWM) assay. A 10 cm escape platform was submerged 1 cm below the water surface into a circular plastic pool filled up with opaque water. Three visual cues were positioned on the walls around the pool. A digital camera was installed above the center of the maze. Images will be acquired and transmitted to a PC running the tracking software ANY-maze (ANY-maze). On the first three days (pre-training) the mice were trained using a visible platform (the platform was placed above the water surface).

To assess spatial memory formation, the mice were trained to locate the hidden platform for 8 consecutive days. The escape latency of each trial (4 per day with an interval of 3-5 min) was recorded and analyzed by the tracking software. At training day 3 and at day 9, memory retention was assessed in a probe trial performed by removing the platform and analyzing the search pattern used by each mouse for a fixed time of 45 seconds.

Figure 3B:
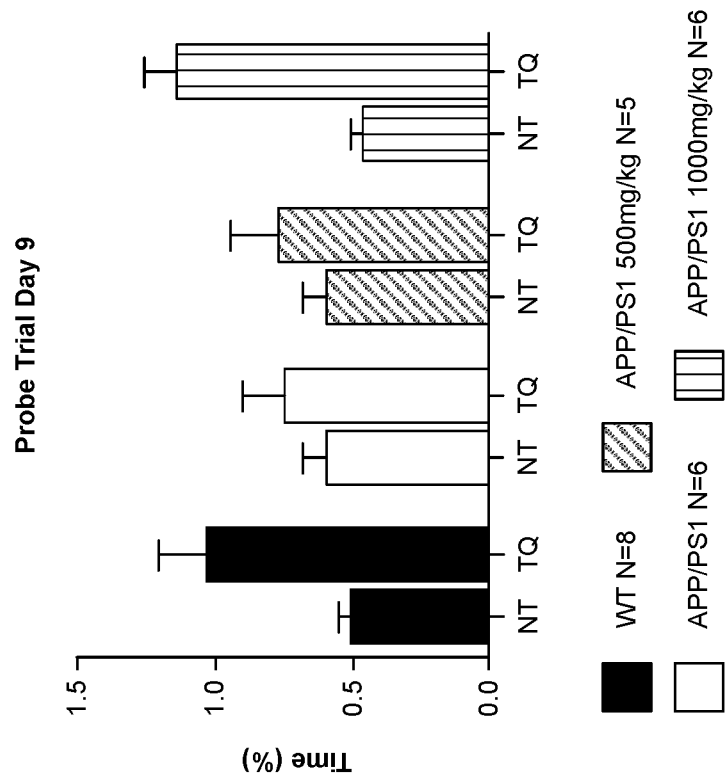
FIG. 3B shows the mean time (%) of mice in the three non-target quadrants (NT) and the time (%) of mice in the target quadrant (TQ), in probe trial on day 9, of wildtype mice, APP/PS1 mice, APP/PS1 mice treated with 500 mg/kg/day of dapansutrile, and APP/PS1 mice treated with 1000 mg/kg/day of dapansutrile.
Figure 3A:
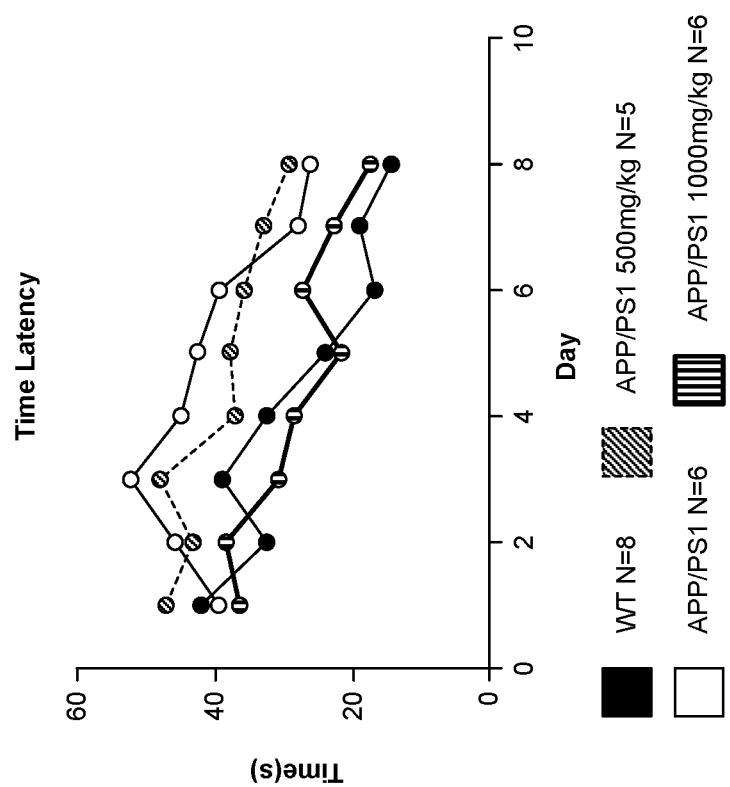
FIG. 3A shows the time latency (seconds) of escape in the Morris water maze test from day 1 to day 8 of wildtype mice, APP/PS1 mice, APP/PS1 mice treated with 500 mg/kg/day of dapansutrile, and APP/PS1 mice treated with 1000 mg/kg/day of dapansutrile.

The escape latency which describes the time mice need to find the hidden platform was measured and was analyzed as the mean value of the 4 trials each day and shown in FIG. 3A; all genotypes decreased the escape latency from day 1 to day 8. For example, on day 5, wildtype mice (N=8) needed 23.59±4.08 seconds to reach the platform. APP/PS1 (500 mg/kg/day dapansutrile treated) mice (N=5) needed 37.31±4.96 seconds, and APP/PS1 (1000 mg/kg dapansutrile treated) mice (N=6) needed 21.30±3.19 seconds (p value=0.021), compared to APP/PS1 (control food) mice (n=6) needed 42.04±6.89 seconds.

To provide the evidence for cognitive learning 24 hours after the last training session, a reverence test was performed (probe trial) on training day 9. Here, mice were tested in the water maze without the platform to escape and the time was measured in which quadrant the mice spend their time. We compare the mean time in percentage of the three non-target quadrants (NT) to the time in percentage of the target quadrant (TQ, platform was located during training period). The results (FIG. 3B) show a significant preference for the target quadrant (TQ) over non-target quadrants (NT) in wildtype mice, p value=0.001, and in APP/PS1 1000 mg/kg/day (medium dose), p value=0.0001. Whereas there was no preference for a TQ over NT in APP/PS1 (control food) and APP/PS1 500 mg/kg/day (low dose).

In summary, FIGS. 3A and 3B show that APP/PS1 control mice had cognitive learning deficits in the performance of Morris water Maze test compared with wildtype mice. In contrast, APP/PS1 mice treated with 1000 mg/kg/day of dapansutrile performed as good as wildtype mice.

Example 6

Electrophysiological Experiments

Long-term potentiation (LTP) is a persistent increase in synaptic strength following high-frequency stimulation of a chemical synapse. Studies of LTP are often carried out in slices of the hippocampus, an important organ for learning and memory. In such studies, electrical recordings are made from cells and plotted in a graph, which compares the response to stimuli in synapses that have undergone LTP versus synapses that have not undergone LTP. Synapses that have undergone LTP tend to have stronger electrical responses to stimuli than other synapses.

Given the observed recovery in the impaired learning and memory processes in APP/PS1 mice treated with 1000 mg/kg/day dapansutrile (Example 5), we were interested in determining whether hippocampal network function would be recovered following medium dose of dapansutrile administration. For this purpose, we analyzed synaptic plasticity at the Schaffer collateral pathway connecting the CA3 with the CA1 subfield, one of the most extensively studied synapses in the central nervous system. Long-term potentiation (LTP) as a cellular correlation of learning processes at the Schaffer collateral CA3 to CA1 pathway was induced by theta-burst stimulation (TBS) after 20 min of baseline recording.

Acute hippocampal slices were prepared from mice in four groups including wild-type, APP/PS1, APP/PS1 treated with 500 mg/kg/day and APP/PS1 treated with 1000 mg/kg/day of dapansutrile. Briefly, mice were deeply anesthetized with 100% $CO_2$, killed, and then brains were quickly removed and transferred into ice-cold carbogenated (95% $O_2$ and 5% $CO_2$) artificial CSF (ACSF) solution. Afterward, the hippocampus was dissected and transverse hippocampal slices (400 µm) were obtained using a manual tissue chopper. The hippocampal slices were transferred to an interface recording chamber, where they were incubated at 32° C. with a constant flow rate (0.5 ml/min) of carbogenated ACSF for 2 h before the start of recordings. Field excitatory post synaptic potentials (fEPSPs) were recorded in the stratum radiatum of the CA1 region in hippocampal slices. Responses were evoked by stimulation of the Schaffer collateral pathway using two electrodes. These stimulation electrodes (S1 and S2) were positioned equidistantly on both sides of the recording electrode and, by this means, two independent stimulation pathways could be used for the same CA1 recording region. For recording fEPSPs (measured as the first slope function), the recording electrode was placed in the CA1 apical dendritic layer and signals were amplified by a differential amplifier and digitized. An input-output curve (afferent stimulation vs fEPSP slope) for assessment of basal synaptic transmission was generated after the pre-incubation period. Test stimulation intensity was modified to be adjusted to extract fEPSP slope as 40% of the maximal fEPSP response for both synaptic inputs S1 and S2. To investigate LTP, 20 min after baseline recording, LTP was induced by theta-burst stimulation (TBS) including four bursts at 100 Hz repeated 10 times in a 200 ms interval. This stimulation was repeated three times in a 10 s interval. Only healthy sections with a stable baseline were included in the electrophysiological data analysis. The slope of fEPSPs was measured over time for 60 min and normalized to the baseline. Data acquisition and offline analysis were performed using IntraCell software.

Figure 4:
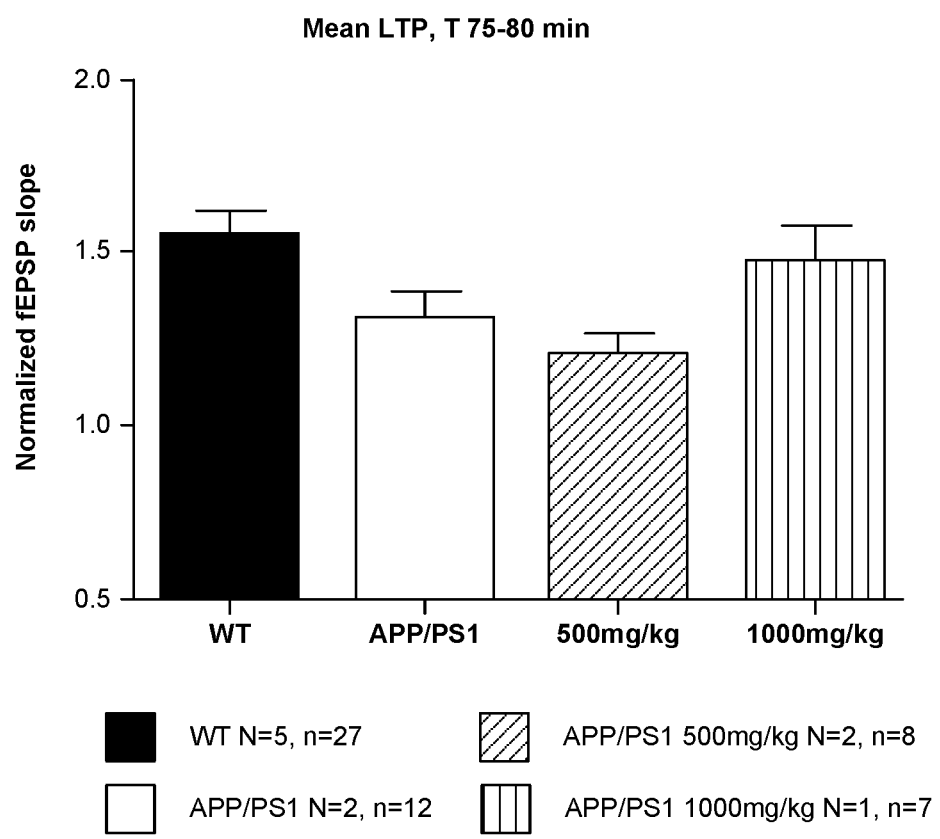
FIG. 4 shows mean LTP at time 75-80 min, which was 55-60 min after TBS induction, and was the last 5 minutes of recording, of wildtype mice, APP/PS1 mice, APP/PS1 mice treated with 500 mg/kg/day of dapansutrile, and APP/PS1 mice treated with 1000 mg/kg/day of dapansutrile. N=number of animals, and n=number of hippocampus slices.

Mean LTP at time 55-60 min after TBS, which was the last 5 minutes of recording, of different groups of mice are shown in FIG. 4. N=numbers of mice, and n=number of hippocampal slices. The normalized mean LTP of last 5 minutes of recording for wildtype mice (N=5, n=27) was 1.553, for APP/PS1 mice (N=2, n=12) was 1.303, for APP/PS1 mice treated with low dose dapansutrile was 1.198 (N=2, n=8) and with medium dose (N=1, n=7) was 1.469. The LTP impairment in APP/PS1 mice was rescued following treatment of 1000 mg/kg/day dose of dapansutrile. However, the low dose dapansutrile (500 mg/kg/day) administration was not able to improve the LTP deficit in APP/PS1 mice.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A method for treating Alzheimer's disease, comprising the step of:

administering to a subject in need thereof an effective amount of dapansutrile, or a pharmaceutically acceptable solvate thereof.

2. The method according to claim 1, wherein said method reduces neuroinflammation in the subject.

3. The method according to claim 1, wherein said method improves the cognitive functions of the subject.

4. The method according to claim 1, wherein said method improves learning and memory processes of the subject.

5. The method according to claim 1, wherein dapansutrile is administered to the subject every 1-3 days for 3 months to 5 years.

6. The method according to claim 1, wherein dapansutrile is administered to the subject 100-2000 mg/day.

7. The method according to claim 1, wherein the subject is identified by family history, generic screening, clinical signs of memory loss, and/or brain scan.

8. The method according to claim 1, wherein said compound is administered by systemic administration.

9. The method according to claim 8, wherein said compound is administered by oral administration.

10. The method according to claim 1, comprising administering to the subject an effective amount of dapansutrile.

\* \* \* \* \*